United States Patent [19]

Lester

[11] E Patent Number: Re. 33,642

[45] Reissued Date of Patent: Jul. 23, 1991

[54] NEBULIZER WITH CAPILLARY FEED

[75] Inventor: Victor E. Lester, Sonora, Calif.

[73] Assignee: Hudson Oxygen Therapy Sales Company, Temecula, Calif.

[21] Appl. No.: 257,197

[22] Filed: Oct. 13, 1988

Related U.S. Patent Documents

Reissue of:

[64] Patent No.: 4,512,341
Issued: Apr. 23, 1985
Appl. No.: 443,473
Filed: Nov. 22, 1982

U.S. Applications:

[63] Continuation of Ser. No. 876,777, Jun. 20, 1986, abandoned.

[51] Int. Cl.[5] ..... A61M 16/00

[52] U.S. Cl. ..... 128/200.21; 128/200.18; 239/338

[58] Field of Search ..... 128/200.18, 200.21, 128/200.14; 239/338

[56] References Cited

U.S. PATENT DOCUMENTS

| | | | |
|---|---|---|---|
| 2,993,652 | 7/1961 | Curry | 239/338 |
| 3,172,406 | 3/1965 | Bird et al. | 128/200.21 |
| 3,762,409 | 10/1973 | Lester | 128/200.14 |
| 3,826,255 | 7/1974 | Havstad et al. | 128/200.21 |
| 3,999,713 | 12/1976 | Lindsey | 239/338 |
| 4,566,451 | 1/1986 | Badewien | 128/200.21 |
| 4,566,452 | 1/1986 | Farr | 128/200.18 |

FOREIGN PATENT DOCUMENTS

| | | | |
|---|---|---|---|
| 1046264 | 12/1958 | Fed. Rep. of Germany | 239/338 |

*Primary Examiner*—Max Hindenburg
*Assistant Examiner*—J. D. Lacyk
*Attorney, Agent, or Firm*—Jerry R. Seiler

[57] ABSTRACT

A nebulizer in which the feed to the spray nozzle is through a narrow space between the flat bottom of the liquid reservoir and a flange fixed to the bottom of the spray nozzle, where the space is narrow enough to draw liquid toward the spray nozzle by capillary action and aspiration at any orientation of the nebulizer between vertical and horizontal.

8 Claims, 2 Drawing Sheets

NEBULIZER WITH CAPILLARY FEED

Matter enclosed in heavy brackets [ ] appears in the original patent but forms no part of this reissue specification; matter printed in italics indicates the additions made by reissue.

*This is a continuation of co-pending application Ser. No. 06/876,777, filed on June 20, 1986 now abandoned.*

BACKGROUND OF THE INVENTION

Nebulizers are devices used to introduce fine droplets of liquid into a flowing stream of air that is to be inhaled. Nebulizers are usually used to medicate a patient's lungs.

Among other things, an effective nebulizer must produce droplets of liquid of the right size. If the liquid droplets are too big they plate out on equipment or even in the trachea or bronchial tubes of the patient and as a result insufficient medication reaches the patient's lungs. On the other hand, if the droplets are too small they do not deposit in a patients lungs and are exhaled, and the patient does not receive sufficient medication.

Most nebulizers are connected in series with a device to supply pressurized air to the patient and the nebulizers have a reservoir or sump to contain the liquid medication. If a patient is to be given a measured amount of liquid medication it is necessary for the nebulizer to function so that all of the liquid medication is drained from the reservoir. Otherwise the unused amount must be accounted for. A device having most of the above-noted characteristics is described in U.S. Pat. No. 3,762,409. In the nebulizer described in that patent draining of the reservoir of liquid is accomplished by making the reservoir acorn-shaped so that as the liquid is consumed it is drained toward the converging bottom point of the acorn where the liquid inlet to the nebulizer system is located. With that arrangement substantially all of the liquid medication is introduced into the air supply to the patient if the nebulizer is kept vertical.

In order to minimize the amount of medication that plates out on the walls of the equipment it is important that the nebulizer be located close to the mouthpiece through which a patient inhales medicated air. When a patient using a nebulizer changes position the nebulizer will move from a completely vertical orientation and as a result some breaths of air are not medicated. Also, frequently, the last few drops of liquid medication are not introduced into the inhaled airstream and less than the full dose of medication is provided to the patient.

SUMMARY OF THE INVENTION

This invention is a nebulizer assembly that may be used in any orientation between vertical and horizontal and in any position it will provide a steady and continuous supply of liquid from the reservoir to the portion of the nebulizer creating spray. The device of this invention is simple and may be easily molded from plastic and therefore it can be made inexpensive enough to be disposable.

The device of this invention includes all of the usual elements of a nebulizer built in accordance with U.S. Pat. No. 3,762,409. It includes a liquid reservoir, a spray nozzle, and a gas nozzle positioned within the spray nozzle and spaced from it to provide a flow path for liquid between the reservoir and the spray nozzle. However, in the nebulizer of this invention the reservoir has a flat bottom surface and the spray nozzle has a bottom flange that extends laterally from the spray nozzle and parallel to the flat bottom of the reservoir. The flange preferably extends almost to side wall of the reservoir and it is spaced from the flat bottom of the reservoir less than 0.02 inches. The flange should be as parallel as possible with the flat bottom surface of the reservoir and it functions best if the space between the flange and the reservoir is from 0.02 to 0.002 inches. For liquids of different viscosity, surface tension and other capillary characteristics, the spacing should be changed to provide adequate flow rate. For aqueous liquids a space about 0.005 inches is preferred.

Spacing between the flange and the bottom of the reservoir is preferably provided with pads formed integrally with the bottom of the flange. The pads could also be formed integrally with the bottom of the reservoir, however, it is easier to mold the plastic flange with pads having the proper depth than it is to mold pads on the more complex reservoir portion of a nebulizer.

DETAILED DESCRIPTION OF THE INVENTION

Figure 1:
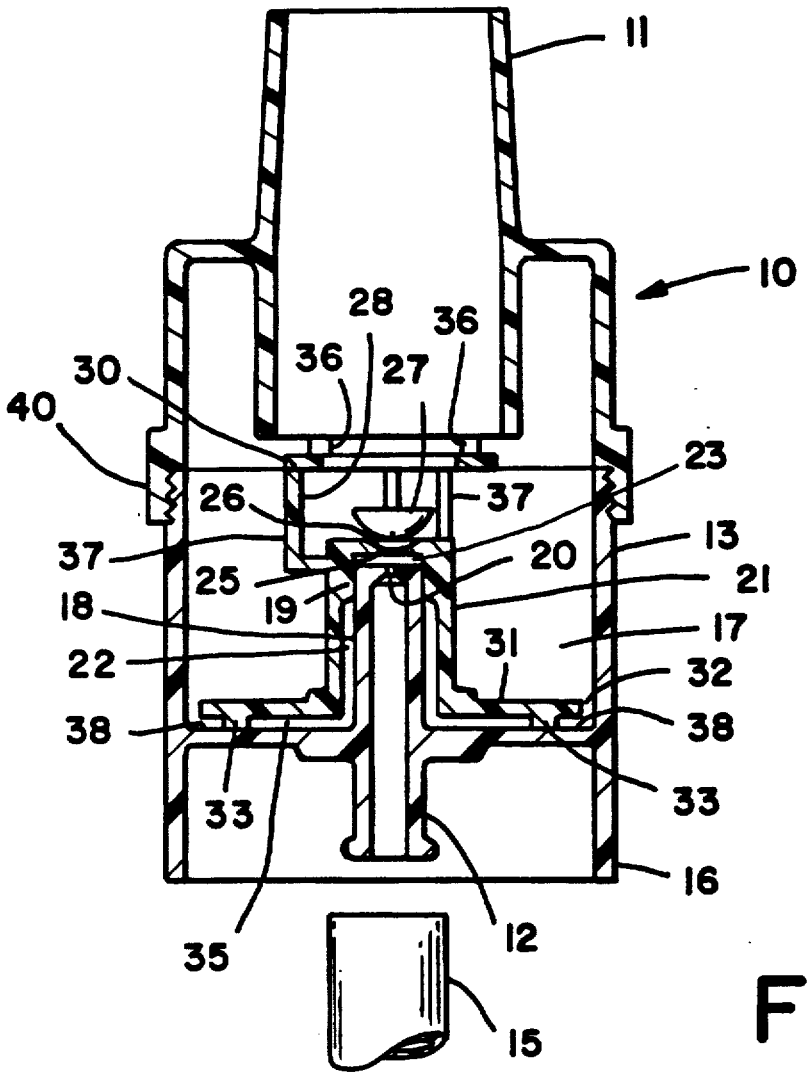
FIG. 1 is a sectional view of a nebulizer embodying this invention.

The device of FIG. 1 is generally designated 10 and it includes an outlet for aerosol 11, an air inlet 12 and a main body 13. An air supply hose 15 is connected to the air inlet 12 when the device is in use. In a preferred embodiment, the body extends to a skirt 16 that protects the air inlet 12.

The body 13 is usually oriented vertically in the position shown in FIG. 1. When so oriented the lower portion 17 forms a reservoir for the liquid that is to be subdivided into the flowing airstream to form the aerosol. The air inlet 12 extends into the body to form a air nozzle 18 that terminates in an orifice 20.

Spray nozzle 21 surrounds air nozzle 18 and is spaced from it by spacers 19 to provide a fluid-flow passageway 22 which opens into a horizontal space 23 between the upper portion of air nozzle 18 and the upper portion of spray nozzle 21. The upper portion of spray nozzle 21 is provided with an orifice 25 that opens into an inverted conical portion 26 into which a rounded diffuser 27 extends. The spacing between the conical portion 26 and the diffuser 27 is important in generating an aerosol in which the particle size is correct. The diffuser's position is established by legs 28 which also hold a baffle plate 30 that knocks out oversized droplets of liquid from the aerosol and returns them to the reservoir 17. Details of how the device illustrated in FIG. 1 functions to produce an aerosol containing droplets of the proper size are disclosed in U.S. Pat. No. 3,762,409.

In the device of this invention, the spray nozzle 21 terminates in a flange 31 that extends almost to the wall surrounding the reservoir 17. The space 32 between the flange 31 and the reservoir wall preferably is quite small, the only limitation being that it is large enough for sufficient liquid to flow from the reservoir 17 toward the orifice 25 so that aerosol can be produced by introducing subdivided liquid into the airstream.

The width of space 23 is established by the relative lengths of air nozzle 18 and spray nozzle 21. Pads 33 on the bottom of flange 31 not only establish the width of capillary passageway 35 but also the width of space 23. The baffle plate 30 performs the function of knocking oversized droplets of liquid from the aerosol and performs the further function of engaging legs 37, which are connected to spray nozzle 21 thereby forcing the entire spray nozzle assembly downwardly to maintain pads 33 in contact with the flat bottom 38 of the reservoir. Baffle plate 30 is held in position by spacers 36 that are located between aerosol outlet 11 and baffle plate 30 to form a rigid connection between them. The device is made into segments that are held together with a threaded connection generally designated 40.

In operation, the nebulizer is connected to a breathing apparatus for a patient by connecting aerosol outlet 11 into a tee in an air supply line to the patient's mouthpiece. Devices known to the art supply air at regulated pressure and volume to a mouthpiece through which the patient breathes. Through means known to the art compressed air is supplied through tube 15 and into air inlet 12 during the inhalation cycle of the patient's breathing while that compressed air is cut off during the exhalation cycle of the patient's breathing. When compressed air is supplied through tube 15 to the air inlet 12, it passes through air nozzle 18 and through orifice 20. Orifice 20 is somewhat smaller than orifice 25 and as a result it creates an aspiration effect drawing liquid from reservoir 17 through gap 32 and space 35 whereby the liquid rises through fluid-flow passageway 22, space 23 and is drawn into the airstream passing through orifice 25. The liquid is subdivided as a result of entering the high velocity airstream and is further subdivided when it impinges against diffuser 27 and is forced through the venturi-shaped passageway between rounded diffuser 27 and the inverted conical portion 26. The resultant aerosol impinges against baffle plate 30 and as a result of the impingement, larger droplets are coalesced and fall back into reservoir 17 while droplets of the proper size 40 remain entrained in air, pass around baffle plate 30 and discharge through aerosol outlet 11 whereupon the aerosol enters the air supplied to the patient for breathing. The capillary passageway 35, in accordance with this invention, is a maximum of 0.02 inches wide and is preferably between 0.01 inches and 0.002 inches wide. When the liquid in reservoir 17 is aqueous this dimension should be about 0.005 inches whereby, as will be discussed hereinafter, the liquid in reservoir 17 is drawn into the capillary passageway 35 by the combination of capillary action and aspiration and is available to enter fluid-flow passageway 22 when the device of this invention is in any orientation between vertical and horizontal.

Figure 2:
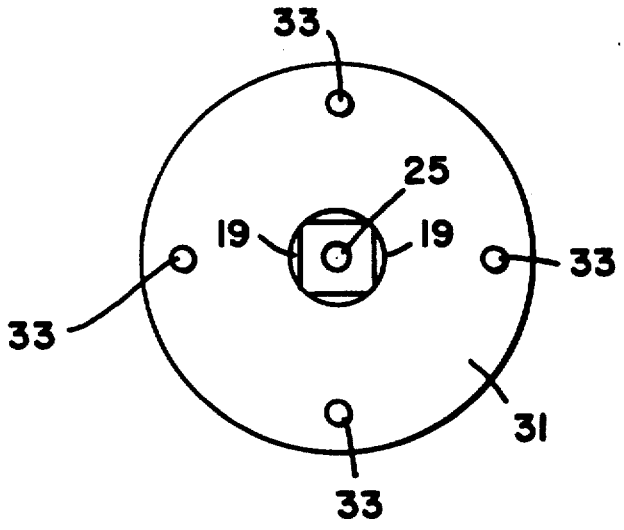
FIG. 2 is a bottom view of the spray nozzle illustrated in FIG. 1.

FIG. 2 is a bottom view of the spray nozzle 21 and its attached flange 31. FIG. 2 illustrates one particular arrangement of pads 33 on the bottom of the flange and spacers 19 within the spray nozzle.

Figure 3:
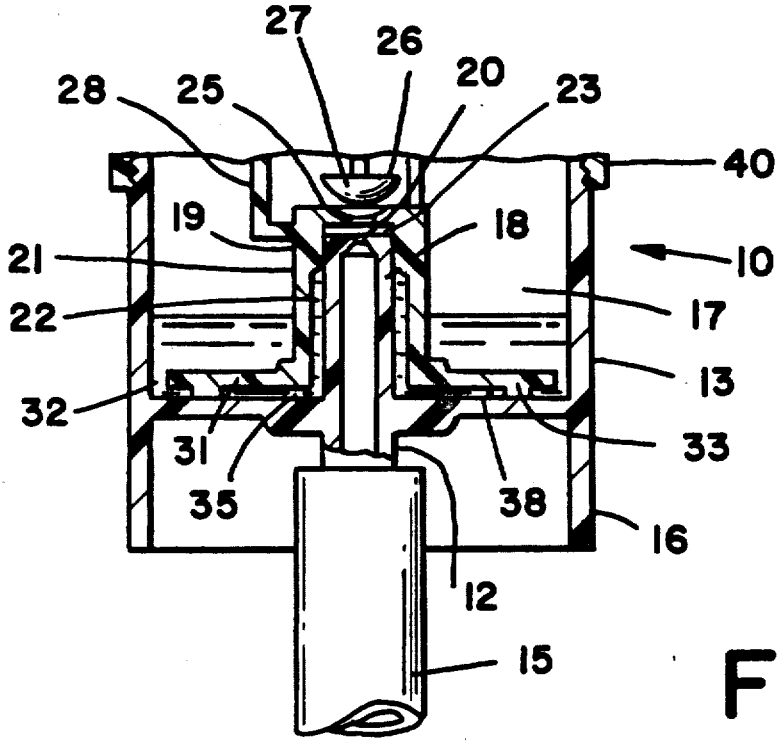
FIG. 3 is a partial sectional view of the nebulizer illustrated in FIG. 1 illustrating the lower portion of the reservoir filled with liquid when the nebulizer is vertically oriented.
Figure 4:
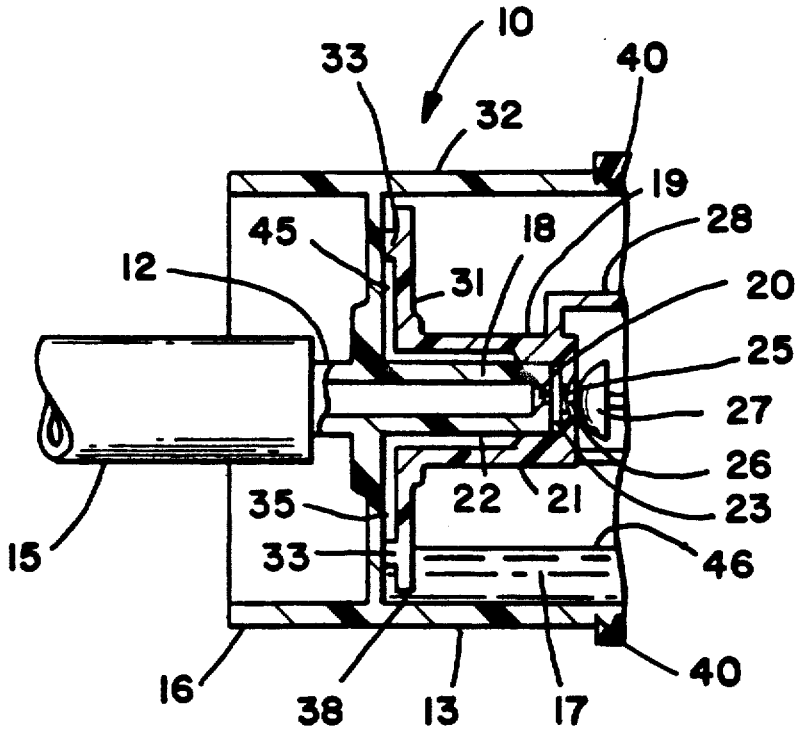
FIG. 4 is the view of FIG. 3 when the nebulizer is horizontally oriented.

FIG. 3 is a partial sectional view of the device illustrating it with air tube connected and with liquid in the reservoir. In FIG. 3 the device is vertically oriented and it is evident that with the capillary passageway 35 completely beneath the surface of liquid, there is a continuous supply of liquid to the bottom of fluid flow passageway 22. FIG. 4 illustrates the same partial view of the device of this invention in a horizontal orientation. Here the liquid in reservoir 17 does not completely surround capillary passageway 35. However, when capillary passageway 35 has the critical dimensions set forth above, it will provide enough capillary action to draw the liquid from reservoir 17 to a level such that it may be aspirated into fluid-flow passageway 22. The level of liquid in the capillary space is at 45 even though the level of liquid in the reservoir is at 46.

What is claimed is:

1. In a nebulizer having a reservoir for liquid, outlet means from said reservoir, a gas nozzle extending along the longitudinal axis of said reservoir, gas inlet means connected to said gas nozzle, a liquid spray nozzle mounted relative to said gas nozzle for nebulization of liquid sprayed from said spray nozzle, and liquid passageway means extending between said reservoir and said spray nozzle to provide a liquid flow path therebetween, wherein the improvement in said nebulizer comprises:

said reservoir including a bottom wall [extending substantially normal to said longitudinal axis and] formed to extend laterally across a lower side of said reservoir to a side wall;

said passageway means including a fluid-flow conduit extending from said spray nozzle and terminating in an opening positioned proximate and above said bottom wall; and said passageway means further including a collector flange extending laterally outwardly from said conduit around said opening to substantially the greatest width dimension of said reservoir and terminating proximate said side wall with the periphery of said flange and said side wall defining an annular collector opening, said flange being mounted in spaced relation to said bottom wall at a distance not more than 0.02 inches to define a capillary passageway between said bottom wall and said flange.

2. The nebulizer as defined in claim 1, wherein said reservoir is substantially cylindrical with a flat end providing said bottom wall, said fluid-flow conduit is in substantially perpendicular relationship to said bottom wall, and said flange is provided as a disk-like member extending over substantially the entire area of said bottom wall in parallel relation thereto to define a capillary passageway in substantially perpendicular orientation to said fluid-flow conduit.

3. The nebulizer of claim 1 wherein the space between the flange and the nebulizer is between 0.02 and 0.002 inches.

4. The nebulizer of claim 3 wherein said space is about 0.005 inches.

*5. In a nebulizer having a reservoir for liquid, outlet means from said reservoir, a gas nozzle extending along the longitudinal axis of said reservoir, gas inlet means connected to said gas nozzle, a liquid spray nozzle mounted relative to said gas nozzle for nebulization of liquid sprayed from said spray nozzle, and liquid passageway means extending between said reservoir and said spray nozzle to provide a liquid flow path therebetween, wherein the improvement in said nebulizer comprises:*

*said reservoir including a bottom wall extending substantially normal to said longitudinal axis and formed to extend laterally across a lower side of said reservoir to side wall;*

*said passageway means including a fluid-flow conduit extending from said spray nozzle and terminating in an opening positioned proximate and above said bottom well; and*

*said passageway means further including a collector flange extending laterally outwardly from said conduit around said opening to substantially the greatest width dimension of said reservoir and terminating proximate said side wall with the periphery of said flange and said side wall defining an annular collector opening, said flange being mounted in spaced relation to said bottom wall at a distance not more than 0.02 inches to define a capillary passageway between said bottom wall and said flange.*

*6. The nebulizer as defined in claim 5, wherein said reservoir is substantially cylindrical with a flat end providing said bottom wall,*

*said fluid-flow conduit is in substantially perpendicular relationship to said bottom wall, and*

*said flange is provided as a disk-like member extending over substantially the entire area of said bottom wall in parallel relation thereto to define a capillary passageway in substantially perpendicular orientation to said fluid-flow conduit.*

*7. The nebulizer of claim 5 wherein the space between the flange and the nebulizer is between 0.02 and 0.002 inches.*

*8. The nebulizer of claim 7 wherein said space is about 0.005 inches.*

* * * * *